United States Patent
Wolter

(10) Patent No.: US 6,974,461 B1
(45) Date of Patent: Dec. 13, 2005

(54) FIXATION SYSTEM FOR BONES

(76) Inventor: Dietmar Wolter, c/o Berufsgenossenschaftliches, Unfallkrankenhaus, Bergedorfer Strasse 10, D-21033, Hamburg (DE)

(*) Notice: Subject to any disclaimer, the term of this patent is extended or adjusted under 35 U.S.C. 154(b) by 190 days.

(21) Appl. No.: 10/070,863

(22) PCT Filed: Sep. 14, 2000

(86) PCT No.: PCT/EP00/09118

§ 371 (c)(1), (2), (4) Date: Jul. 8, 2002

(87) PCT Pub. No.: WO01/19268

PCT Pub. Date: Mar. 22, 2001

(30) Foreign Application Priority Data

Sep. 14, 1999 (DE) .................. 199 43 924
Dec. 23, 1999 (DE) .................. 199 62 317

(51) Int. Cl.$^7$ .............................................. A61B 17/58
(52) U.S. Cl. ...................................................... 606/69
(58) Field of Search .................... 606/67–71

(56) References Cited

U.S. PATENT DOCUMENTS

| | | | | |
|---|---|---|---|---|
| 4,338,926 A | * | 7/1982 | Kummer et al. | 606/70 |
| 5,147,361 A | | 9/1992 | Ojima et al. | 606/61 |
| 5,306,275 A | | 4/1994 | Bryan | 606/61 |
| 5,558,674 A | | 9/1996 | Heggeness et al. | 606/61 |
| 5,620,445 A | | 4/1997 | Brosnahan et al. | 606/63 |
| 5,785,713 A | * | 7/1998 | Jobe | 606/69 |
| 6,342,055 B1 | * | 1/2002 | Eisermann et al. | 606/69 |
| 6,468,278 B1 | * | 10/2002 | Muckter | 606/69 |

FOREIGN PATENT DOCUMENTS

| | | |
|---|---|---|
| DE | 43 43 117 A1 | 6/1995 |
| DE | 196 29 011 AQ | 1/1998 |
| DE | 198 58 889 A1 | 6/2000 |
| EP | 0 201 024 | 4/1986 |
| FR | 742618 | 12/1931 |

* cited by examiner

Primary Examiner—Glenn K. Dawson
Assistant Examiner—D. Jacob Davis
(74) Attorney, Agent, or Firm—Vidas, Arrett & Steinkraus, P.A.

(57) ABSTRACT

A fixation system for bones with a force support having holes and bone screws adapted to be inserted into the holes where at least one hole is oriented obliquely to the force support.

9 Claims, 2 Drawing Sheets

US 6,974,461 B1

FIXATION SYSTEM FOR BONES

CROSS-REFERENCE TO RELATED APPLICATIONS

Not Applicable

STATEMENT REGARDING FEDERALLY SPONSORED RESEARCH

Not Applicable

BACKGROUND OF INVENTION

The invention relates to a fixation system for bones with a force support having holes and bone screws which are insertable into the holes.

If fragments of broken bones have to be joined to each other plate, nail and fixateur systems are available nowadays. Stability in plate and nail systems has been reached hitherto by the fact that if osteosynthetic plates were used bone screws firmly pulled these plates up to the bones in order to achieve a stabilization of the fragments of broken bones by means of the contact pressure which the plate exerts on the bones. If a marrow nail is used which is in the marrow space stability will also be increased by transversely inserting screws through the bone and the marrow nail. Although these screws are located in the bone by a thread minor motions are possible because the screw passes through the nail.

Different technical solutions were successful in fixedly joining the head of the screw to the plate or to establish a fixed connection between the screw and the marrow nail itself. In this respect, reference is made to EP 0 201 024 B1, DE 43 43 117 A1, DE 196 29 011 A1, and the German Patent Application P 198 58 889.5.

Hence, it is proper to speak of inner fixateur systems in this new generation of implants because the main feature of the outer fixateurs is angular stability between the screw and the transverse force support.

In clinical applications, these fixateur systems have distinctly exhibited a superiority over conventional plate and nail systems up to now.

Holes are oriented perpendicularly to the force support in known fixation systems.

However, if the patient loads the implant with too much of his body weight too early, which is contrary to a doctor's advice, the implant might be spoiled by bending or the implant might break.

It has been observed that if bones are soft and/or are subjected to high loads, particularly by bending, the screws might be torn out of the bone.

FR-A-742 618 discloses obliquely oriented holes in connecting pieces for osteosynthesis. The holes have threads the thread axis of which exactly coincides with the hole axis. Moreover, the connecting pieces have a thickened material region adjacent to the holes. The consequence is that the bone screws can only be inserted in an exactly coaxial relationship with the hole axis. As a result, only unidirectional stability is achieved and the implant involves expenditure in manufacture.

More implants having obliquely directed holes and uni-directionally insertable bone screws have been known from U.S. Pat. No. 5,306,275, U.S. Pat. No. 5,147,361, and U.S. Pat. No. 558,674.

Accordingly, it is the object of the invention to provide a fixation system for bones which allows to simplify its manufacturing technique and to introduce bone screws in an optimal angular orientation in the bones.

BRIEF SUMMARY OF THE INVENTION

The invention relies on the surprising finding that the there are optimal positions of the bone screws depending on the bone region in order to make the anchoring of the force support, which can particularly be an implant, as favourable as possible in the bone. First and foremost, the positions concerned are those in which the bone screws would exhibit an oblique orientation to the force support or to that portion of the force support which substantially extends in parallel with the bone or bone region in which the bone screw is desired to be anchored. Therefore, the fixation system for bones having a force support with holes and with bone screws adapted to be inserted into the holes have at least one hole which is oriented obliquely to the force support. This means that the hole has a hole axis which is obliquely oriented at least to that portion of the force support through which the hole extends. As a result, a bone screw inserted into the hole may be given an optimal position in the bone region associated therewith. In addition or instead, the fixation system may have at least one hole oriented perpendicularly to the force support, but particular measures which will be explained below still enable a bone screw to be oriented obliquely to the force support in this hole. The advantages of the invention are particularly conspicuous in the bone regions close to the joint. As a rule, the bone is widened here. An insertion of the bone screws which is oblique to the force support will cause a more favourable fixation here. A better load transfer and stabilization of the fragments of broken bones will be achieved altogether. This can also have an effect as a reduced load acting on the fixation system and help avoid its distortion or breakage.

Basically, it is possible for the fixation system to have at least one hole which is oriented obliquely to the force support and at least one hole which is oriented perpendicularly to the force support in a conventional manner. However, all of the holes may be in an oblique orientation to the force support as well. The hole axes of the various holes may be at different angles to the force support here. Further, all of the holes can be oriented perpendicularly to the force support.

It is particularly advantageous to join the bone screw and force support in an angularly stable fashion.

According to a solution, at least one hole has at least one element which is deformable by turning in a bone screw and which extends approximately in a plane oriented obliquely to the hole axis of the hole. The deformable element, in particular, may be a lip, a ridge, an edge or a thread as above. In particular, the element concerned can also be hole oriented obliquely to the force support. For example, it will then be possible to achieve particularly small angles between the bone screw and the force support. However, the bone may also be a hole oriented perpendicularly to the force support. The oblique orientation of the deformable element will then allow to fix a bone screw in an oblique orientation to the force support also in such a hole. The orientability of the bone screw required to be secured here by an appropriate configuration of the hole.

According to a further solution, at least one hole has a thread for turning in a bone screw the thread axis of which is oriented obliquely to the hole axis. This makes it possible again, for example, for holes oriented obliquely to the force support to achieve a particularly small angle of the bone screw towards the force support. In contrast, if the hole is oriented perpendicularly to the force support a position of the bone screw which is optimally oblique can be achieved in the bone.

To achieve a screwed joint which is angularly stable, a deformable element or a thread may also be on the bone screw, i.e. in addition to the arrangement in the hole according to one of the above aspects a or also in lieu of it.

All of the angularly stable joints mentioned above can have the deformable element or thread formed, for example, in a hole which expands conically or spherically or a portion thereof and/or at the underside of a screw head of the bone screw which is to be inserted into the hole. If the hole has an adjoining cylindrical portion the diameter thereof may be dimensioned such that it allows to obliquely orient a shank of the bone screw therein. This also applies to the solutions and aspects which follow.

As far as the angularly stable joints have a deformable element these allow to turn in the bone screw at different angular positions with respect to the force support. This can be utilized, in particular, for a precise adjustment of the bone screw in the bone. This will be dealt with later below.

One aspect is based on the surprising finding that bone screws are susceptible to extraction particularly if they are introduced into the bone in parallel with each other. To avoid such exiting from the bone, at least two holes are made into the force support which are not in parallel with each other, but are obliquely inclined towards each other. In exchange, at least one hole may be obliquely inclined towards the force support as compared to conventional force supports in which the holes are made at an angle of 90° from the force support (or from a central plane or a supporting plane thereof on the bone). Preferably, two or more holes can be disposed in an appropriately inclined fashion towards each other. It is preferred here that holes which require to be disposed on different sides of a zone of fracture or instability of a bone are disposed so as to be inclined towards each other in different directions. The straddled position of the bone screws in the bone tissue allows to improve the transfer of loads.

Since the bone, as a rule, has curved surfaces and this is the case particularly in the area close to joints it is necessary that plate systems, in particular, be adapted to such bone curvatures. As a rule, this operation is accomplished by appropriate bending tools during the surgery. It is also possible here to vary the orientation of plate holes in accordance with the conformation. If a distinct bone surface curvature is found, e.g. in the area close to joints, the screw hole if obliquely placed may make it even easier to achieve an optimal screw position in the bone. This can be taken into account from the very beginning in orienting holes in the plate so that a desired oblique orientation of at least two holes is achieved in the plate upon conformation.

The bone screws are adapted to be inserted into the holes of the force support under different angles and to be fixed therein. The force support and the screws can be configured here according to the patent applications mentioned at the beginning, particularly according to DE 43 43 117 A1, DE 196 29 011 A1 or P 198 58 889.5. In particular, the fixation of the screws at different angles in the force support may be served by a deformable element which is located in the hole and/or on the screw and which may be a ridge, a lip, an edge or a thread. While the bone screw is turned into the hole with the material experiencing deformation it is possible to achieve different angular orientations of the bone screw in the force support. At this stage, for example, orientability can be achieved within a range of angles of from 10° to 15° with respect to the hole axis. Even higher angle degrees are achievable with the expenditure for material deformation, however, being larger. An optimized orientation of the hole or the element to be deformed which is predetermined already may make it easier for the operator to bring the screw to an optimal position without deforming a lot of material in the bone hole.

If at least two holes in the force support are inclined obliquely to each other it is possible, from the very beginning, to insert at least two bone screws into the force support in a position inclined to each other without using up the clearance provided by the fixability under different angles. This significantly improves the possible ways to make the screws straddle in the bone because of an inclined position.

The fixation system may specifically be a bone plate, a bone nail or a fixateur in the two solutions.

The oblique orientation of the hole or the deformable element or the thread with respect to the force support specifically allows to avoid extracting or damaging the implant when under an excessive stress.

BRIEF DESCRIPTION OF THE SEVERAL VIEWS OF THE DRAWINGS

The invention will now be explained in greater detail with reference to the accompanying drawings of embodiments. In the drawings.

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated.

Figure 1:
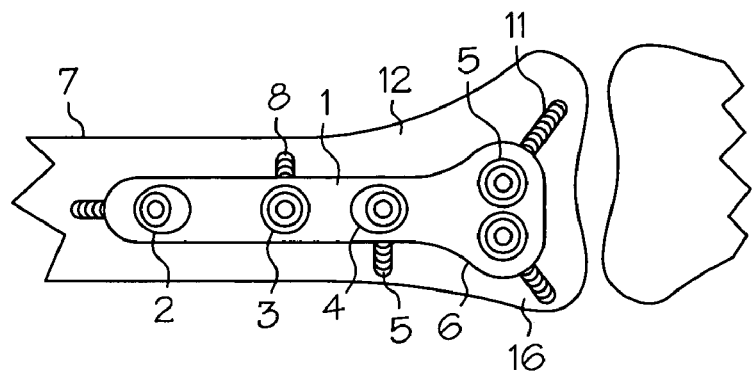
FIG. 1 shows a bone plate on a tibia bone close to a joint in a plan view.

According to FIG. 1, a substantially T-shaped bone plate 1 substantially has three holes 2, 3, 4 in the elongate portion and has two more holes 5, 6 in a short, transversely oriented portion. The holes 2 to 6 have a hole axis each which is disposed obliquely to that portion of the bone plate 1 in which the respective hole 2 to 6 is located. If a bone plate 1 is completely level each hole 2 to 6 has a certain oblique orientation to the plane through the entire bone plate 1.

The holes 2 to 6 has inserted therein bone screws 7, 8, 9, 10, 11 the orientation of which matches to the orientations of the holes 2 to 6. This optimally orients the bone screws 7 to 11 to those regions of a tibia bone 12 into which they need to be turned.

The bone screws 7 to 11 engage their screw heads with the holes 2 to 6.

Figure 2:
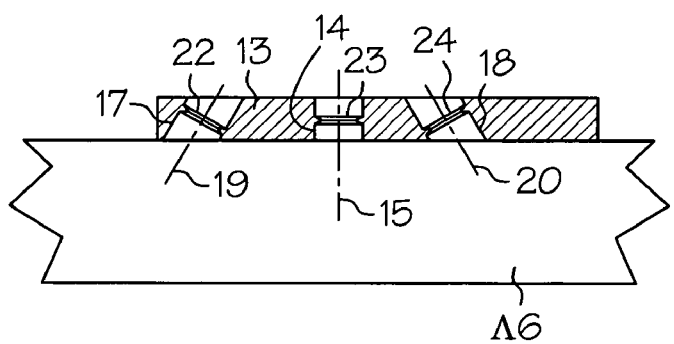
FIG. 2 shows a bone plate having a perpendicular hole and two obliquely oriented holes at the central portion of a tubular bone in a longitudinal section.

FIG. 2 shows a bone plate 13 where the middle hole 14 has conventionally oriented its hole axis 15 perpendicularly to the bone plate 13. As a result, a bone screw turned into the hole 14 will always be turned perpendicularly into a tubular bone 16 which is located below.

However, the two outer holes 17, 18 of the bone plate 13 have their axes 19, 20 oriented at an acute angle towards the bone plate 13. The result is that bone screws to be turned into the two outer holes 17, 18 will caused to straddle in the adjoining bone 16, thus securely fixing the bone plate 13.

Moreover, all of the holes 14, 17, 18 have an element 21, 22, 23 to fix a bone screw, which can be configured as a deformable ridge or lip or edge or as a preformed thread (deformable or not), in an angularly stable fashion. In the example, the element 21, 22, 23 for an angularly stable fixation is disposed in a plane oriented perpendicularly to the hole axis 15, 19, 20 provided that the element 21, 22, 23 concerned is a ridge, a lip or an edge. In case that the element 21, 22, 23 concerned is a thread its axis coincides with the hole axis 15, 19, 20.

If the element 21, 22, 23 for an angularly stable fixation of the bone screws is of a deformable design there is an additional possibility to fix the bone screws in the holes 14, 17, 18 at different orientations with regard to the hole axes 15, 19, 20. To this effect, the bone screws have their screw heads inserted into the holes, 14, 17, 18 with threads at the undersides of the screw heads interacting with the deformable elements 21, 22, 23.

Figure 3:
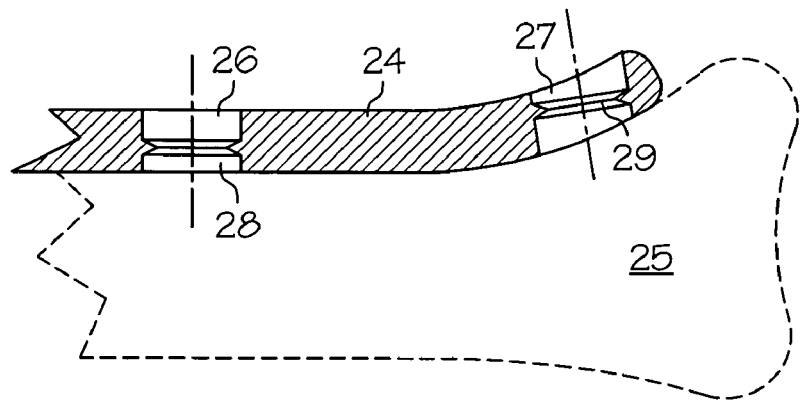
FIG. 3 shows a curved bone plate on a tibia bone close to a joint in a partial longitudinal section.

In FIG. 3, a bone plate 24 has been deformed by undergoing bending so as to fit well to the joint region of a tibia bone 25. It has holes 26, 27. There can be more holes on the cut-away part of the bone plate 24. The axis of the hole 26 is oriented perpendicularly to the bone plate 24. The axis of the hole 27 is inclined, from the very beginning, with respect to the bone plate 24 or its support area on the bone 25. To this effect, the axis of the hole 27 is shaped so as to provide an oblique orientation of the axes of holes 26, 27 towards each upon conformation of the bone plate 24 to the bone 25. The result is that the screws which were turned in will straddle in the bone 25, which counteracts the bone plate 24 being torn out of the bone 25.

In FIG. 3, the holes 26, 27 of the bone plate 24 are provided with a circumferential ridge 28, 29 at their inner periphery. A bone screw having a thread at the underside of its head may be turned into this ridge 28, 29, which causes a deformation of the ridge 28, 29 depending on the angle at which the bone screw is turned in with respect to the axis of the hole 26, 27. In addition, while the ridge or the thread of the screw undergoes deformation the screw is secured in its turned-in position in the bone. The pre-planned oblique position of the axes of holes 26, 27 with respect to each other allows to inclinedly orient the bone screws towards each other without using up the clearance existing for fixability under different angles in the bone plate 24. Thus, what is simultaneously achieved are a straddled position and an optimal orientability of the bone screws in an individually optimizable angular position in their holes 26, 27.

Figure 4:
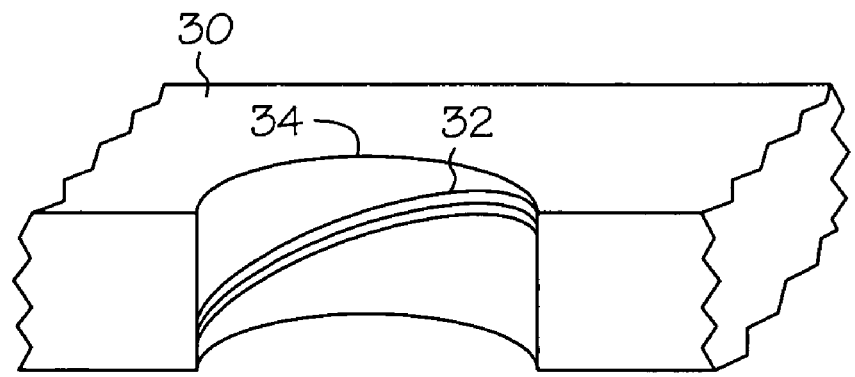
FIG. 4 shows a bone plate having a perpendicularly oriented hole and a deformable element in an obliquely oriented plane in a perspective portion.

In FIG. 4, it is true that the bone plate 30 has a hole 31 which is conventionally oriented as being perpendicular to the plate. However, there is at least one element 32 in the hole 31 for an angularly stable fixation of a bone screw, which element is oriented obliquely to the hole axis of the hole 31. In particular, the element 32 may be a deformable ridge, lip or edge and will then be disposed in a plane which is inclined obliquely to the hole axis. However, the element 32 in question may also be a preformed thread the thread axis of which is inclined with respect to the hole axis. In either case, the element allows to anchor a screw in a predetermined oblique orientation towards the bone plate 30 with a certain additional variation of the angular positions being possible if the element 32 is designed as being deformable.

Figure 5:
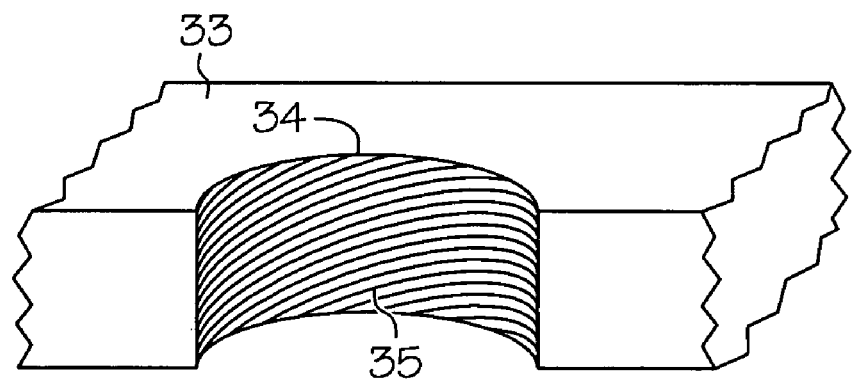
FIG. 5 shows a bone plate having an obliquely oriented hole and a preformed thread in a perspective partial portion.

In FIG. 5, a bone plate 33 has a hole 34 which is oriented obliquely to it from the very beginning and is provided with a preformed thread 35. A bone screw can be turned into the hole 34 in a predetermined orientation which is oblique to the bone plate 33. In addition, a certain angular orientability may be provided in a deformable design of the thread 35.

Also in the embodiments of FIGS. 4 and 5, it is preferred that the bone screw has its screw head anchored in the respective hole 31, 34. To this end, the screw head may taper off towards the top, i.e. that side of the bone plate 30, 33 which faces away from the bone.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A fixation system for bones comprising:
    a force support having
        a posterior surface and an anterior surface;
    at least two holes in the force support each having an axis; and
    at least two bone screws each having
        a screw head portion and a non-head portion;
    wherein the bone screws are adapted to be inserted into the holes,
    where at least one hole has at least one deformable element which can become deformed by turning a bone screw into a hole,
    whereby the deformable element fixes a bone screw into a hole,
    where the deformable element is one selected from the group consisting of:
    a ridge, a lip or and an edge,
    and where the deformable element extends in a plane oriented obliquely to the axis of the hole.

2. The fixation system according to claim 1, wherein at least one hole is oriented perpendicularly to the force support.

3. The fixation system according to claim 1, wherein at least one hole is oriented obliquely to the force support.

4. The fixation system according to claim 1, wherein at least two holes are oriented obliquely towards each other.

5. The fixation system according to claim 4, wherein the axes of two holes diverge and are further apart on the posterior surface of the force support than on the anterior surface.

6. The fixation system according to claim 1, wherein the force support is formed according to the surface of an area of a bone.

7. The fixation system according to claim 1, wherein a screw head portion and a non-head portion of the bone screw are comprised of materials with different degrees of hardness.

8. The fixation system according to claim 1 wherein the force support is one selected from the group consisting of: a bone plate, a bone nail, and a fixateur.

9. The fixation system according to claim 1, wherein the force support is conformable to the surface of a bone.

* * * * *